United States Patent [19]

Larsen

[11] 4,091,815
[45] May 30, 1978

[54] FLEXIBLE TUBE CLAMP

[76] Inventor: Otis M. Larsen, 4036 Reservoir Blvd., Minneapolis, Minn. 55421

[21] Appl. No.: 702,488

[22] Filed: Jul. 6, 1976

[51] Int. Cl.² .............................................. A61B 17/12
[52] U.S. Cl. .............................. 128/325; 24/132 WL; 24/134 R; 128/346; 251/10
[58] Field of Search ............. 24/134 E, 136 B, 250 R, 24/250 HE, 258, 263 B, 263 LS, 134 R, 132 WL; 128/325, 346; 251/9, 10

[56] References Cited

U.S. PATENT DOCUMENTS

| 249,610 | 11/1881 | Glazier et al. | 24/250 R X |
| 586,359 | 7/1897 | Holt | 24/250 R UX |
| 1,297,456 | 3/1919 | Frey | 251/10 |
| 1,513,367 | 10/1924 | Brix | 128/246 |
| 1,557,396 | 10/1925 | Ayres et al. | 24/258 |
| 1,852,542 | 4/1932 | Sovatkin | 128/346 X |
| 2,589,511 | 3/1952 | Redmon | 24/250 R X |
| 2,622,837 | 12/1952 | Goodman | 251/9 |
| 3,247,852 | 4/1966 | Schneider | 128/325 UX |
| 3,256,579 | 6/1966 | Hoover | 251/9 |
| 3,531,835 | 10/1970 | Paikin | 24/250 R |
| 3,612,047 | 10/1971 | Nesbit | 128/79 |

Primary Examiner—Robert W. Michell
Assistant Examiner—Michael H. Thaler
Attorney, Agent, or Firm—Merchant, Gould, Smith, Edell, Welter & Schmidt

[57] ABSTRACT

The disclosure is directed to a clamp for flexible tube and more particularly a clamp for surgical use. The clamp is formed of plastic material and has a pair of clamping members connected by a flexible hinge. The flexible hinge biases the clamping members open and a cam with at least one elongated handle closes the clamping members about a flexible tube or vessel. The clamp may be locked by a screw threaded through the cam and which is advanceable into contact with one clamping member. The clamping members are provided with beveled edges to define narrow convex clamping surfaces for the concentrated distribution of the clamping force, and the surfaces have serrations to prevent slippage of the tube from the grasp of the clamp. The clamping members may be curved to facilitate insertion of the clamp into inaccessible body areas during surgical applications.

12 Claims, 10 Drawing Figures

U.S. Patent  May 30, 1978  4,091,815
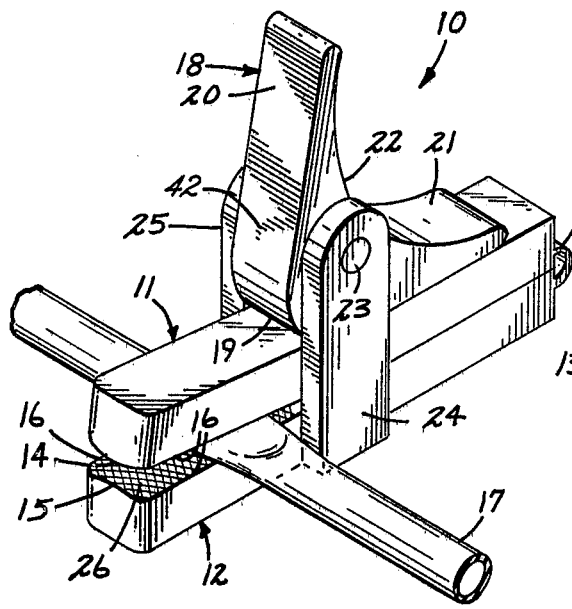
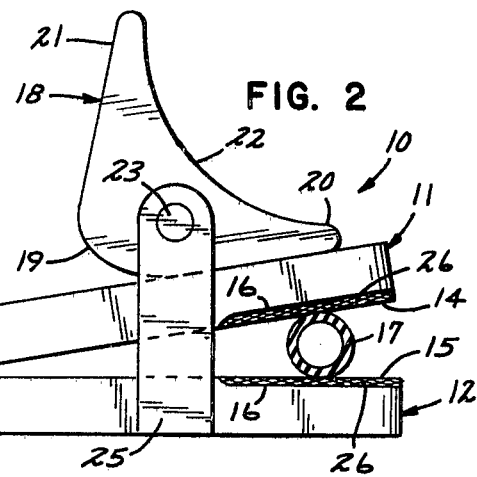
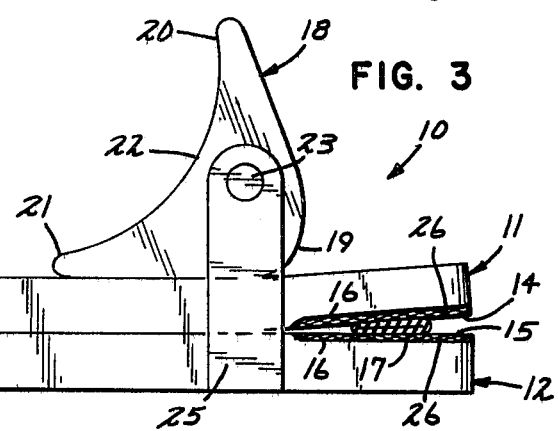
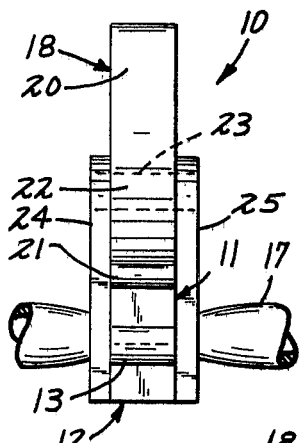
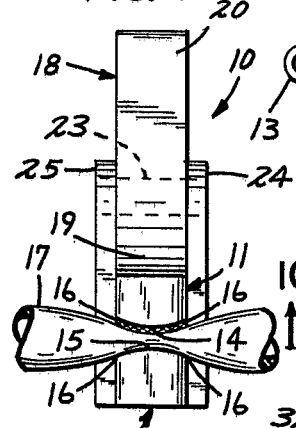
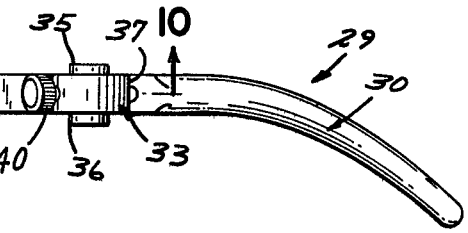
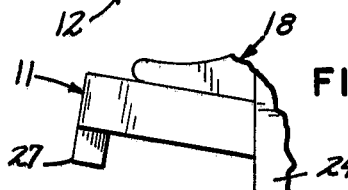
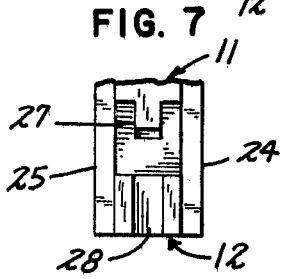
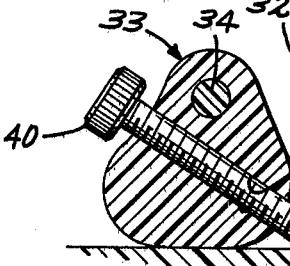
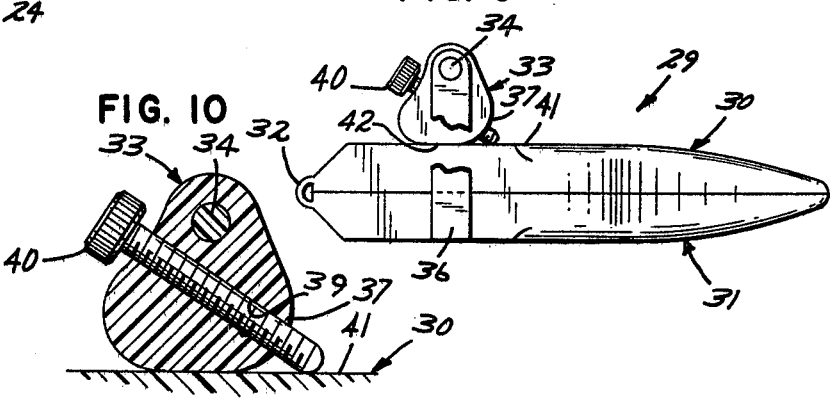

FLEXIBLE TUBE CLAMP

BACKGROUND OF THE INVENTION

This invention relates to clamps for flexible tubes and more particularly to clamps for use in surgical applications.

Clamps for shutting off the flow of fluid through flexible tubing are of particular importance, for example, in regulating the flow of intravenous fluids and in surgical applications requiring blood vessels to be closed to minimize blood loss. With respect to flexible tubing outside the body the clamps must be designed to effectively block the flow of fluids and prevent the inadvertent opening of the clamp. During surgery, a clamp must be capable of being efficiently and quickly placed on a blood vessel and structured so that the vessel will not slip from the grasp of the clamp. In some instances, the clamps must be left in the body for extended periods of time requiring that the clamp be formed of a material compatible with body tissues.

Various clamps are currently in use, the most typical of which is a wire wound metal clamp spring biased in the clamping or closing position so that the clamp must be open for the insertion of a tube therein. Flexible plastic tubing has a tendency to slip from the grasp of such clamps creating unnecessary complications and requiring constant attention.

U.S. Pat. No. 2,463,451 (Yates) discloses a U-shaped flexible clamp with clamping surfaces at the free ends of the clamping members. The clamp is biased open and closed by an elongated handle having a cam surface contacting one of the clamping members. The clamping surfaces in Yates are broad pads which would tend to distribute the clamping force over a wide area. Such a distribution is undesirable in applications wherein a tube or vessel must be completely closed to fluid flow. Additionally, the Yates clamp may be inadvertently opened by the accidental manipulation of the handle.

Additionally, U.S. Pat. No. 3,766,925 (Rubricius) and 3,162,475 (Dinger) each discloses a surgical clamp molded of plastic material. These clamps are difficult to utilize in internal body areas that are relatively inaccessible since the surgeon must grasp the clamp about its tube clamping portion to effectively place the clamp. The Rubricius device is also impractical where the vessel to be clamped is not one that has been cut. The placement of the Rubricius clamp about such a vessel requires the complex manipulation of its parts.

The prior art, thus, does not overcome all the problems associated with clamps for flexible tubes, as in dialysis applications, or with clamps for surgical use to block blood flow in vessels.

The present invention overcomes these problems in that it is a cam-actuated positive locking clamp easily manipulatable by an operator using a single hand. Further, it has serrations along the clamping surface to prevent slippage of the flexible tubes. The clamp is provided with a locking device to prevent the accidental opening of the clamp. Additionally, the clamp may have elongated curved clamping members to facilitate insertion of the clamp into relatively inaccessible internal body locations.

SUMMARY OF THE INVENTION

The present invention is a clamp having upper and lower clamping members, a hinge biasing the clamping members open, a cam mounted on a shaft which is pivotally retained by a pair of posts secured to the lower clamping member and which has a cam surface contacting the upper clamping member, and a screw member threaded through the cam and advanceable into contact with the upper clamping member to lock the clamp in place. The clamping surfaces have beveled edges and are convex to form a narrow tube grasping area for concentrated pressure application. The clamping surfaces also have serrations which more effectively grasp the flexible tube and prevent slippage of the tube from the clamp.

Additionally, the clamping members have a mating projection and recess at their outer ends which serve to prevent slipping of the tube through the clamping ends.

In an alternative embodiment, the clamping members are curved along their longitudinal axis and tapered to facilitate insertion of the clamp about body organs into relatively inaccessible locations.

BRIEF DESCRIPTION OF THE DRAWINGS

FIG. 1 is a perspective view of one embodiment of the present invention;

FIG. 2 is a side elevation of the invention disclosed in FIG. 1 showing the clamp in the open position;

FIG. 3 is a side elevation of the invention shown in FIG. 1 illustrating the clamp in the clamping position;

FIG. 4 is a rear elevation of the invention disclosed in FIG. 1 showing the invention in the clamping position;

FIG. 5 is a front elevation of the clamp disclosed in FIG. 1 in the clamping position;

FIG. 6 is a partial side elevation of the invention disclosed in FIG. 1 illustrating the lock positioned at the end of the clamping members;

FIG. 7 is also a partial front elevation showing the engagement of the lock illustrated in FIG. 6;

FIG. 8 is a plan view of an alternative embodiment of the present invention illustrating curved clamping members;

FIG. 9 is a side elevation of the invention disclosed in FIG. 8; and

FIG. 10 is an enlarged sectional view of the invention along line 10—10 of FIG. 8 and illustrates a locking apparatus for retaining the clamp in the clamping position.

DETAILED DESCRIPTION OF THE INVENTION

Referring initially to FIGS. 1 through 5, wherein like numerals represent like parts of one embodiment, a clamp designated generally as 10 has a pair of clamping members 11 and 12 which are connected at one end by a hinge 13. In the preferred embodiment, hinge 13 is a formed strip of resilient material integral with the clamping members. Preferably, the clamp is made entirely of a plastic material compatible with body tissue in order for the clamp to be left within a patient's body for extended periods of time without adversely affecting the patient. The resilient hinge normally biases the clamping members open. Cooperating clamping surfaces 14 and 15 are disposed at the end of the clamping members opposite the hinge. The clamping surfaces are defined in part by beveled edges 16 extending along the longitudinal edge of clamping members 11, 12, and which form a narrow tube pinching surface providing a concentrated distribution of the clamping force against the walls of a tube 17. The tube 17 is shown inserted between the clamping surfaces, and manipulation of the clamp operates to either pinch the walls of the tube together or allow the tube to remain open for fluid flow therethrough as requirements demand.

The clamp is actuated by a cam member 18 having a curved cam surface 19 and two elongated handle means 20 and 21 which define a curved surface 22 against which pressure is applied to operate the clamp. In addition, cam member 18 includes a flat cam surface portion 42 extending from curved surface portion 19, in trailing relationship thereto when cam member 18 is rotated toward the closed position shown in FIG. 3. The cam member is pivotable about a shaft 23 which passes through the cam member along an axis off-center with respect to the central axis of the cam member. The shaft 23 is retained in a pair of posts 24 and 25 which extend upward and parallel to each other from the base clamping member.

As shown in FIG. 1, the clamping surfaces are provided with slight serrations 26 to facilitate grasping of the flexible tube and to prevent slippage of the tube from between the ends of the clamping members. In the application as blood vessel clamps, the serrations are sufficiently slight such that damage to the vessel tissue is eliminated.

The rotation of the cam in the counterclockwise direction from that shown in FIG. 2 closes the clamp to the position shown in FIG. 3. The clamp is operated by grasping the clamping members between the thumb and middle fingers and manipulating the cam handle with the index finger. When curved cam surface portion 19 is rotated into contact with clamping member 11, member 11 is urged toward a closed position with member 12. When trailing flat surface portion 42 is rotated into contact with member 11, cam member 18 is no longer free to rotate without the benefit of direct manipulation of the cam handle, and is thus temporarily secured.

FIGS. 4 and 5 are end views showing the clamp in the tube pinching or closed position pressing the walls of the tube 17 together. As illustrated more particularly in FIG. 5, the clamping surfaces 14, 15 may be convex to define a narrow distribution of the clamping force.

As shown in FIG. 6, the tube or vessel is prevented from slipping through the end of the clamping members by a projection 27 attached to the upper clamping member 11 and which is received in a recess 28 defined in the lower clamping member 12. When the clamp pinches the tube the projection fits within the recess to prevent removal of the tube through the ends of the clamping members. FIG. 7 more specifically illustrates, in an end view, the relationship of the upper clamping member projection 27 and the receiving recess 28 in the lower clamping member.

In some surgical applications it is necessary to utilize a blood vessel clamp in a position within the body which is relatively inaccessible due to the position of adjacent body tissues and organs. The clamp 29 illustrated in FIGS. 8 and 9 is an alternative embodiment of the present invention designed specifically for such surgical applications. The clamp has a pair of clamping members 30, 31 connected by a resilient hinge 32 which biases the clamping members open. The clamping members 30, 31 are curved longitudinally to facilitate insertion of the clamp around body tissues and organs. As shown in FIG. 9 the clamping members 30, 31 may also be tapered toward their vessel clamping ends.

Secured to the clamping member 31 is a pair of posts 35, 36. A cam 33 is eccentrically mounted on a shaft 34 retained in the posts 35, 36. The cam is pivotable about the posts and has a cam surface 37 contacting the upper clamping member 30 to urge the clamping members together. The cam 33 may have an elongated handle similar to handles 20 and 21 of the first embodiment.

Additionally, as more particularly shown in FIG. 10, the cam member 33 has a threaded aperture 39 which receives a screw 40. The screw may be rotated so that it extends through the cam to contact the top surface 41 of the upper clamping member 30. In this position, the screw prevents the rotation of the cam about its pivot thus locking the clamp in place and preventing the inadvertent release of the clamp. The screw locking device may also be utilized in the first embodiment of the invention.

It is apparent from the above description that either embodiment of the present invention is easily manipulatable by an operator using only one hand. The clamping surfaces are narrow to concentrate the tube pinching pressure. Additionally, the serrations provided on the clamping surfaces of either embodiment more effectively retain the tube between the clamping members. Finally, the screw locks the clamp against accidental release.

What is claimed is:

1. A clamp comprising:
   first and second clamping members having cooperating clamping surfaces;
   hinge means connecting said clamping members at one end thereof;
   a pair of posts secured to said first clamping member;
   rotatable cam means eccentrically mounted on a shaft pivotally retained by said posts and having a curved cam surface portion which may be rotated into contact with said second clamping member for urging said clamping members together to a closed position, and said cam means further having a flat cam surface portion extending from and trailing said curved surface portion, which may be rotated into contact with said second clamping member to prevent free rotation of the cam when the clamping members are in the closed position;
   a screw threaded into said cam and
   advanceable through said curved cam surface portion into contact with said second clamping member to secure said clamping members in the closed position.

2. A clamp in accordance with claim 1 wherein said hinge further comprises:
   a strip of resilient material formed integrally with said clamping members and biasing said clamping members apart into an open position.

3. A clamp in accordance with claim 1 wherein said clamping surfaces are formed having serrations thereon.

4. A clamp in accordance wth claim 3 wherein said clamping surfaces have beveled edges along the longitudinal periphery of said clamping surfaces.

5. A clamp in accordance with claim 3 wherein said clamping surfaces are convex.

6. A clamp in accordance with claim 3 further comprising:
   a projection at the clamping end of one of said clamping members which is received in a recess defined in the clamping end of the other of said clamping members.

7. A surgical clamp comprising:
   first and second clamping members having clamping surfaces which are curved longitudinally to facilitate insertion of the clamp into relatively inaccessible body areas;

hinge means for connecting said clamping members at one end thereof;

a pair of posts secured to said first clamping member;

rotatable cam means eccentrically mounted on a shaft pivotally retained by said posts and having a curved cam surface portion rotatable into contact with said second clamping member for urging said clamping members together to a closed position, said curved cam surface portion being trailed by a flat cam surface portion rotatable into contact with said second clamping member for preventing free rotation of said cam means.

8. A surgical clamp in accordance with claim 7 wherein said hinge means further comprises:

a strip of resilient material formed integrally with said clamping members and biasing said clamping members apart to an open position.

9. A surgical clamp in accordance with claim 7 wherein said clamping surfaces have serrations thereon.

10. A surgical clamp in accordance with claim 9 wherein said clamping members are tapered toward their clamping ends.

11. A surgical clamp in accordance with claim 7 further comprising a screw threaded into said clamping member and advanceable into contact with said second clamping member to lock said clamp in the closed position.

12. A surgical clamp in accordance with claim 11 wherein said cam means has at least one elongated handle.

* * * * *